(12) United States Patent
Hoffmann et al.

(10) Patent No.: US 10,166,394 B1
(45) Date of Patent: Jan. 1, 2019

(54) DEVICE AND METHOD TO AUTOMATICALLY TUNE THE NERVE STIMULATION PATTERN OF A SENSORY-FEEDBACK CAPABLE PROSTHESIS

(71) Applicant: HRL Laboratories, LLC, Malibu, CA (US)

(72) Inventors: Heiko Hoffmann, Simi Valley, CA (US); Jaehoon Choe, Agoura Hills, CA (US); Corey M. Thibeault, Encino, CA (US)

(73) Assignee: HRL Laboratories, LLC, Malibu, CA (US)

( * ) Notice: Subject to any disclaimer, the term of this patent is extended or adjusted under 35 U.S.C. 154(b) by 255 days.

(21) Appl. No.: 15/295,657

(22) Filed: Oct. 17, 2016

Related U.S. Application Data

(60) Provisional application No. 62/242,160, filed on Oct. 15, 2015.

(51) Int. Cl.
  *A61N 1/36* (2006.01)
  *A61B 5/11* (2006.01)
  *A61B 5/00* (2006.01)

(52) U.S. Cl.
  CPC ........ *A61N 1/36139* (2013.01); *A61B 5/1104* (2013.01); *A61B 5/1107* (2013.01); *A61B 5/4836* (2013.01); *A61N 1/36003* (2013.01)

(58) Field of Classification Search
  CPC ............ A61N 1/36139; A61N 1/36003; A61B 5/1104; A61B 5/1107; A61B 5/4839
  See application file for complete search history.

(56) References Cited

U.S. PATENT DOCUMENTS

2015/0173918 A1\* 6/2015 Herr .......................... A61F 2/72
623/25

OTHER PUBLICATIONS

Di Pino, G., Guglielmelli, E., & Rossini, P. M. (2009). Neuroplasticity in amputees: main implications on bidirectional interfacing of cybernetic hand prostheses. Progress in Neurobiology. 88(2), pp. 114-126.

Etnyre, B. R. & Abraham, L. D. (1986). H-Reflex Changes During Static Stretching and Two Variations of Proprioceptive Neuromuscular Facilitation Techniques. Electroencephalography and Clinical Neurophysiology, 63, pp. 174-179.

(Continued)

*Primary Examiner* — Paula J Stice
(74) *Attorney, Agent, or Firm* — Tope-McKay & Associates

(57) ABSTRACT

Described is a system for automatically tuning the sensor feedback of a prosthetic device. The system comprises an electrode or plurality of electrodes in contact with a peripheral nerve of a user wearing a prosthetic device for administering the sensory feedback and an additional stimulus that evokes a muscle response in the user. A sensor is used to measure the muscle response. One or more processors generate a current stimulation pattern that encodes a posture of the prosthetic device. The current stimulation pattern is used in a spinal cord simulation to produce predicted muscle activations. Using the muscle response and the predicted muscle activations, an adjusted stimulation pattern is determined.

12 Claims, 6 Drawing Sheets

(56) References Cited

OTHER PUBLICATIONS

Fuhr, P., Cohen, L. G., Dang, N., Findley, T. W., Haghighi, S., Oro, J., & Hallett, M. (1992). Physiological analysis of motor reorganization following lower limb amputation. Electroencephalogr. Clin. Neurophysiol., 85(1), pp. 53-60.

Dhillon, G. S., Krueger, T. B., Sandhu, J. S., Horch, K. W (2005). Effects of Short-Term Training on Sensory and Motor Function in Severed Nerves of Long-Term Human Amputees. Journal of Neurophysiology, 93(5), pp. 2625-2633.

Lavrov, I., Gerasimenko, Y. P., Ichiyama, R. M., Courtine, G., Zhong, H., Roy, R. R., & Edgerton, V. R. (2006). Plasticity of spinal cord reflexes after a complete transection in adult rats: relationship to stepping ability. J Neurophysiol., 96(4), pp. 1699-1710.

Martin, C. E. & Hoffmann, H. (2014). Fast Re-learning of a Controller from Sparse Data. IEEE International Conference on Systems, Man, and Cybernetics, pp. 973-978.

Raphael, G., Tsianos, G. A., & Loeb G. E. (2010). Spinal-like regulator facilitates control of a two-degree-of-freedom wrist. The Journal of Neuroscience, 30(28), pp. 9431-9444.

Rossini, P. M., Micera, S., Benvenuto, A., Carpaneto, J., Cavallo, G., Citi, L., Cipriani, C., et al. (2010). Double nerve intraneural interface implant on a human amputee for robotic hand control. Clinical Neurophysiology. 121(5), pp. 177-783.

Tsianos G. A., Raphael G., & Loeb G. E. (2011). Modeling the potentiality of spinal-like circuitry for stabilization of a planar arm system. Prog. Brain Res. 194, pp. 203-213.

Kirkpatrick, S.; Gelatt Jr, C. D.; Vecchi, M. P. (1983). Optimization by Simulated Annealing. Science 220 (4598): pp. 671-680.

Diamantaras, K. I. and Kung, S. Y. (1996). Principal Component Neural Networks. John Wiley & Sons, New York, pp. 46-51.

Harkema, S., Gerasimenko, Y., Hodes, J., Burdick, J., Angeli, C., Chen, Y., & Edgerton, V. R. (2011). Effect of epidural stimulation of the lumbosacral spinal cord on voluntary movement, standing, and assisted stepping after motor complete paraplegia: a case study. The Lancet, 377(9781), pp. 1938-1947.

Desautels, T. A., Choe, J., Gad, P., Nandra, M. S., Roy, R. R., Zhong, H., & Burdick, J. W. (2015). An Active Learning Algorithm for Control of Epidural Electrostimulation. IEEE Transactions on Biomedical Engineering, 62(10), pp. 2443-2455.

K. Horch, S. Meek, T.G. Taylor, and D.T. Hutchinson. Object discrimination with an artificial hand using electrical stimulation of peripheral tactile and proprioceptive pathways with intrafascicular electrodes. IEEE Transactions on Neural Systems and Rehabilitation Engineering. 19(5): pp. 483-489, 2011.

Weber, D. J, Friesen, R. & Miller, L. E. (2012). Interfacing the Somatosensory System to Restore Touch and Proprioception: Essential Considerations. Journal of Motor Behavior 44 (6), pp. 403-418.

Press, W. H., Teukolsky, S. A., Vetterling, W. T., and Flannery, B. P. (1993). Numerical Recipes in C: The Art of Scientific Computing. Cambridge University Press, UK, pp. 412-420.

\* cited by examiner

DEVICE AND METHOD TO AUTOMATICALLY TUNE THE NERVE STIMULATION PATTERN OF A SENSORY-FEEDBACK CAPABLE PROSTHESIS

CROSS-REFERENCE TO RELATED APPLICATIONS

This is a Non-Provisional application of U.S. Provisional Application No. 62/242,160, filed in the United States on Oct. 15, 2015, entitled, "Device and Method to Automatically Tune the Nerve Stimulation Pattern of a Sensory-Feedback Capable Prosthesis," which is incorporated herein by reference in its entirety.

BACKGROUND OF INVENTION

(1) Field of Invention

The present invention relates to a system for automatic adjustment of neural stimulation for a prosthesis and, more particularly to a system for automatic adjustment of neural stimulation for a prosthesis to provide feedback about the position and posture of the prosthesis.

(2) Description of Related Art

Proprioception is the sense of the position and posture of parts of the body. A major limitation of the prior art is that prosthetic devices with sensory feedback cannot be used at home. All current systems that provide sensory feedback must be adjusted daily by an expert in a laboratory setting. The functional relationship between electrode stimulation and nerve activation varies due to body movement, tissue growth, and adaptation and plasticity of the nervous system (see Literature Reference No. 10 of the List of Incorporated Literature References).

Proprioception is particularly difficult to stimulate; the corresponding nerve fibers are smaller and require lower amplitude stimulations. Moreover, proprioceptive sensation cannot be directly measured, and thus, tuning stimulation parameters is costly, requiring many hours of adjustment. The prior art uses either manual tuning of stimulation parameters or machine learning to adjust the parameters. The machine learning approach uses a Kalman filter to estimate the drift of the stimulation pattern. With both approaches short- and long-term plasticities and variations in the electrode-nerve interface need to be compensated for daily in a laboratory setting with a human "in the loop" (see Literature Reference Nos. 1, 4, and 8). An expert operator is necessary to make adjustments and identify errors, making the whole system unsuitable for at-home use.

Tuning such a system is often a difficult process, as proprioceptive control has been a fundamentally psychobiological problem, and the assessment of the quality of proprioceptive feedback has relied upon qualitative observations and feedback that is impossible to automate. For these reasons, at-home use of prostheses with proprioceptive feedback has not yet been achieved. Thus, a continuing need exists for a system that allows auto-adaptation of stimulation protocols that communicate the proprioceptive information of the prosthesis to the nerve of the affected limb, allowing tuning of the prosthetic outside laboratory settings.

SUMMARY OF INVENTION

The present invention relates to a system for automatic adjustment of neural stimulation for a prosthesis and, more particularly to a system for automatic adjustment of neural stimulation for a prosthesis to provide feedback about the position and posture of the prosthesis. The system comprises an electrode for administering a stimulus to a peripheral nerve of a user wearing a prosthetic device, the stimulus evoking a muscle response in the user; a muscle activation sensor to measure the muscle response; and one or more processors and a memory, the memory being a non-transitory computer-readable medium having executable instructions encoded thereon, such that upon execution of the instructions, the one or more processors perform multiple operations. A current stimulation pattern is applied to the electrode, the current stimulation pattern corresponding to a posture of a prosthetic device of a user. Using the muscle activation sensor, a measured muscle response to the current stimulation pattern is detected. A predicted muscle activation is determined using the current stimulation pattern and the posture of the prosthetic device in a spinal cord simulation. Using the measured muscle response and the predicted muscle activations, the system dynamically determines an adjusted stimulation pattern that compensates for a neuroplastic or hardware change.

In another aspect, a spinal cord model is used to determine the adjusted stimulation pattern.

In another aspect, the muscle response results from a Hoffmann's reflex.

In another aspect, the user moves the prosthetic device into a predetermined posture and then administers the stimulus that evokes the muscle response.

As can be appreciated by one skilled in the art, in another aspect, the present invention also comprises a method for causing a processor to perform the operations described herein.

Finally, in another aspect, the present invention also comprises a computer program product comprising computer-readable instructions stored on a non-transitory computer-readable medium that are executable by a computer having a processor for causing the processor to perform the operations described herein.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

Figure 1:
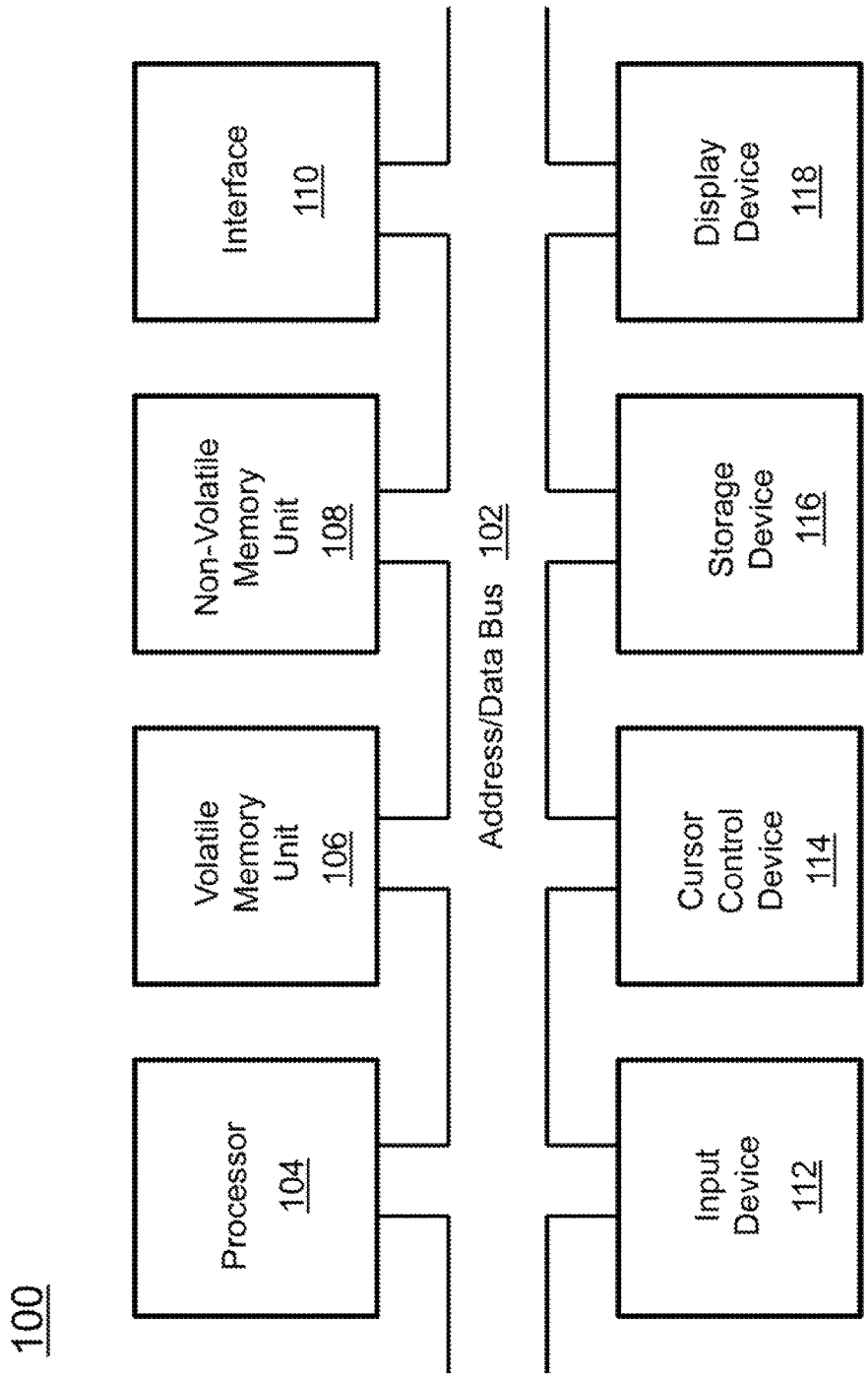
FIG. 1 is a block diagram depicting the components of a system for automatic adjustment of neural stimulation of a prosthesis according to embodiments of the present disclosure.

The present invention relates to a system for automatic adjustment of neural stimulation for a prosthesis and, more particularly to a system for automatic adjustment of neural stimulation for a prosthesis to provide feedback about the position and posture of the prosthesis. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of cited references is provided. Next, a description of the various principal aspects of the present invention is provided. Finally, specific details of various embodiment of the present invention are provided to give an understanding of the specific aspects.

(1) LIST OF CITED LITERATURE REFERENCES

The following references are cited throughout this application. For clarity and convenience, the references are listed herein as a central resource for the reader. The following references are hereby incorporated by reference as though fully set forth herein. The references are cited in the application by referring to the corresponding literature reference number, as follows:

1. Di Pino, G., Guglielmelli, E., & Rossini, P. M. (2009). Neuroplasticity in amputees: main implications on bidirectional interfacing of cybernetic hand prostheses. *Progress in Neurobiology.* 88(2), 114-126.
2. Etnyre, B. R. & Abraham, L. D. (1986). H-Reflex Changes During Static Stretching and Two Variations of Proprioceptive Neuromuscular Facilitation Techniques. *Electroencephalography and Clinical Neurophysiology,* 63, 174-179.
3. Fuhr, P., Cohen, L. G., Dang, N., Findley, T. W., Haghighi, S., Oro, J., & Hallett, M. (1992). Physiological analysis of motor reorganization following lower limb amputation. *Electroencephalogr. Clin. Neurophysiol.,* 85(1), 53-60.
4. Dhillon, G. S., Krueger, T. B., Sandhu, J. S., Horch, K. W. (2005). Effects of Short-Term Training on Sensory and Motor Function in Severed Nerves of Long-Term Human Amputees. *Journal of Neurophysiology,* 93(5), 2625-2633.
5. Lavrov, I., Gerasimenko, Y. P., Ichiyama, R. M., Courtine, G., Zhong, H., Roy, R. R., & Edgerton, V. R. (2006). Plasticity of spinal cord reflexes after a complete transection in adult rats: relationship to stepping ability. *J Neurophysiol.,* 96(4), 1699-710.
6. Martin, C. E. & Hoffmann, H. (2014). Fast Re-learning of a Controller from Sparse Data. *IEEE International Conference on System, Man, and Cybernetics.*
7. Raphael, G., Tsianos, G. A., & Loeb G. E. (2010). Spinal-like regulator facilitates control of a two-degree-of-freedom wrist. *The Journal of Neuroscience,* 30(28), 9431-9444.
8. Rossini, P. M., Micera, S., Benvenuto, A., Carpaneto, J., Cavallo, G., Citi, L., Cipriani, C., et al. (2010). Double nerve intraneural interface implant on a human amputee for robotic hand control. *Clinical Neurophysiology.* 121 (5), 777-783.
9. Tsianos G. A., Raphael G., & Loeb G. E. (2011). Modeling the potentiality of spinal-like circuitry for stabilization of a planar arm system. *Prog. Brain Res.* 194, 203-213.
10. Weber, D. J, Friesen, R. & Miller, L. E. (2012). Interfacing the Somatosensory System to Restore Touch and Proprioception: Essential Considerations. *Journal of Motor Behavior* 44 (6), 403-18.
11. Press, W. H., Teukolsky, S. A., Vetterling, W. T., and Flannery, B. P. (1993). *Numerical Recipes in C: The Art of Scientific Computing.* Cambridge University Press, UK, pages 412-420.
12. Kirkpatrick, S.; Gelatt Jr, C. D.; Vecchi, M. P. (1983). Optimization by Simulated Annealing. *Science* 220 (4598): 671-680.
13. Diamantaras, K. I. and Kung, S. Y. (1996). Principal Component Neural Networks. John Wiley & Sons, New York. Pages 46-51.
14. Harkema, S., Gerasimenko, Y., Hodes, J., Burdick, J., Angeli, C., Chen, Y., & Edgerton, V. R. (2011). Effect of epidural stimulation of the lumbosacral spinal cord on voluntary movement, standing, and assisted stepping after motor complete paraplegia: a case study. The Lancet, 377(9781), 1938-1947.
15. Desautels, T. A., Choe, J., Gad, P., Nandra, M. S., Roy, R. R., Zhong, H., & Burdick, J. W. (2015). An Active Learning Algorithm for Control of Epidural Electrostimulation. IEEE Transactions on Biomedical Engineering, 62(10), 2443-2455.

(2) PRINCIPAL ASPECTS

Various embodiments of the invention include three "principal" aspects. The first is a system for automatic adjustment of neural stimulation of a prosthesis. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
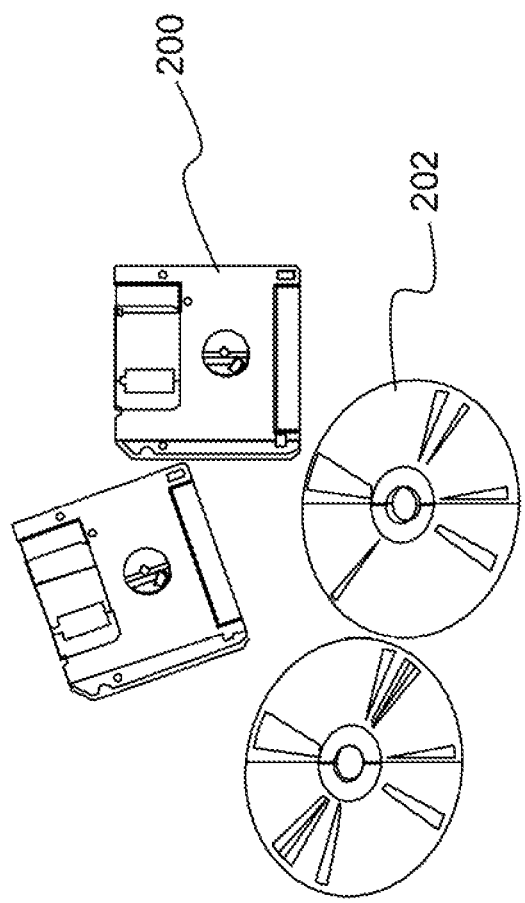
FIG. 2 is an illustration of a computer program product according to embodiments of the present disclosure.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) SPECIFIC DETAILS OF VARIOUS EMBODIMENTS

Figure 3:
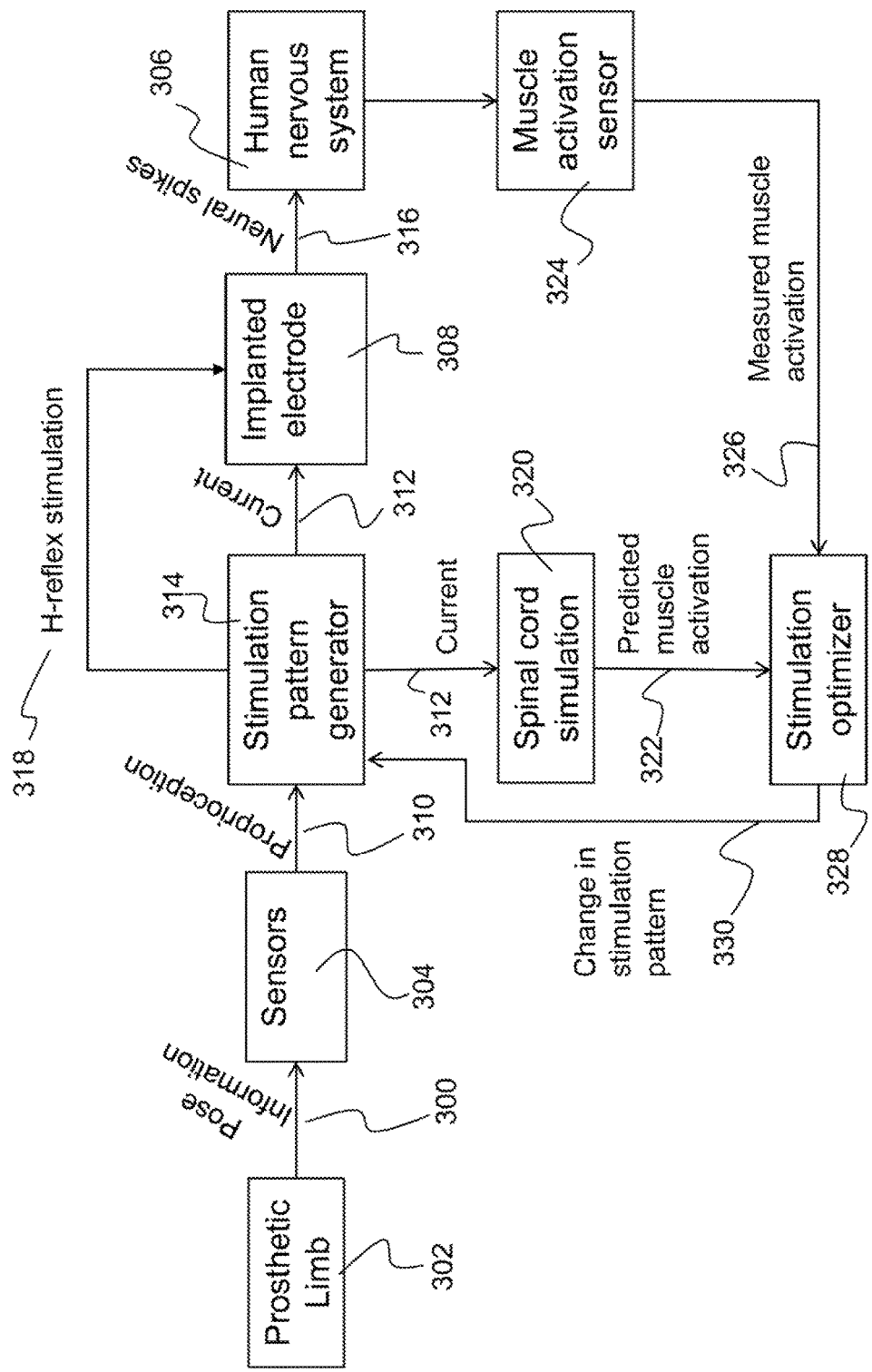
FIG. 3 is a flow chart illustrating the process flow of the system for automatic adjustment of neural stimulation of a prosthesis according to embodiments of the present disclosure.

Described is a system to automatically adjust the sensory feedback of a prosthetic limb. FIG. 3 illustrates the process flow of an embodiment of the present invention. In the depicted embodiment, pose information 300 about the pose of a prosthetic limb 302 (measured via at least one accelerometer or other motion/position sensing apparatus and a pressure/touch sensitive piezoelectric sensor; this is encapsulated as sensor 304) is fed to the human nervous system 306 via an electrode implant 308. The proprioceptive information 310 is transformed into a current stimulation pattern 312 (via a stimulation pattern generator 314), which synthesizes incoming proprioceptive and neural reflex data into appropriate stimulation protocols to provide current stimulation patterns. The current stimulation pattern 312 is then applied to a peripheral nerve of the prostheticized limb (e.g., the ulnar nerve) via the electrode implant 308 causing neural spikes 316. The challenge for this interface is that the interface between electrode implant 308 and nerve (i.e., human nervous system 306) is unstable and, thus, the current stimulation pattern 312 needs to be adjusted dynamically to compensate for ongoing neuroplastic and hardware interface changes that occur throughout the lifetime of the prosthetic appliance. The system according to embodiments of the present disclosure provides an automatic method to adjust this stimulation pattern.

Figure 5:
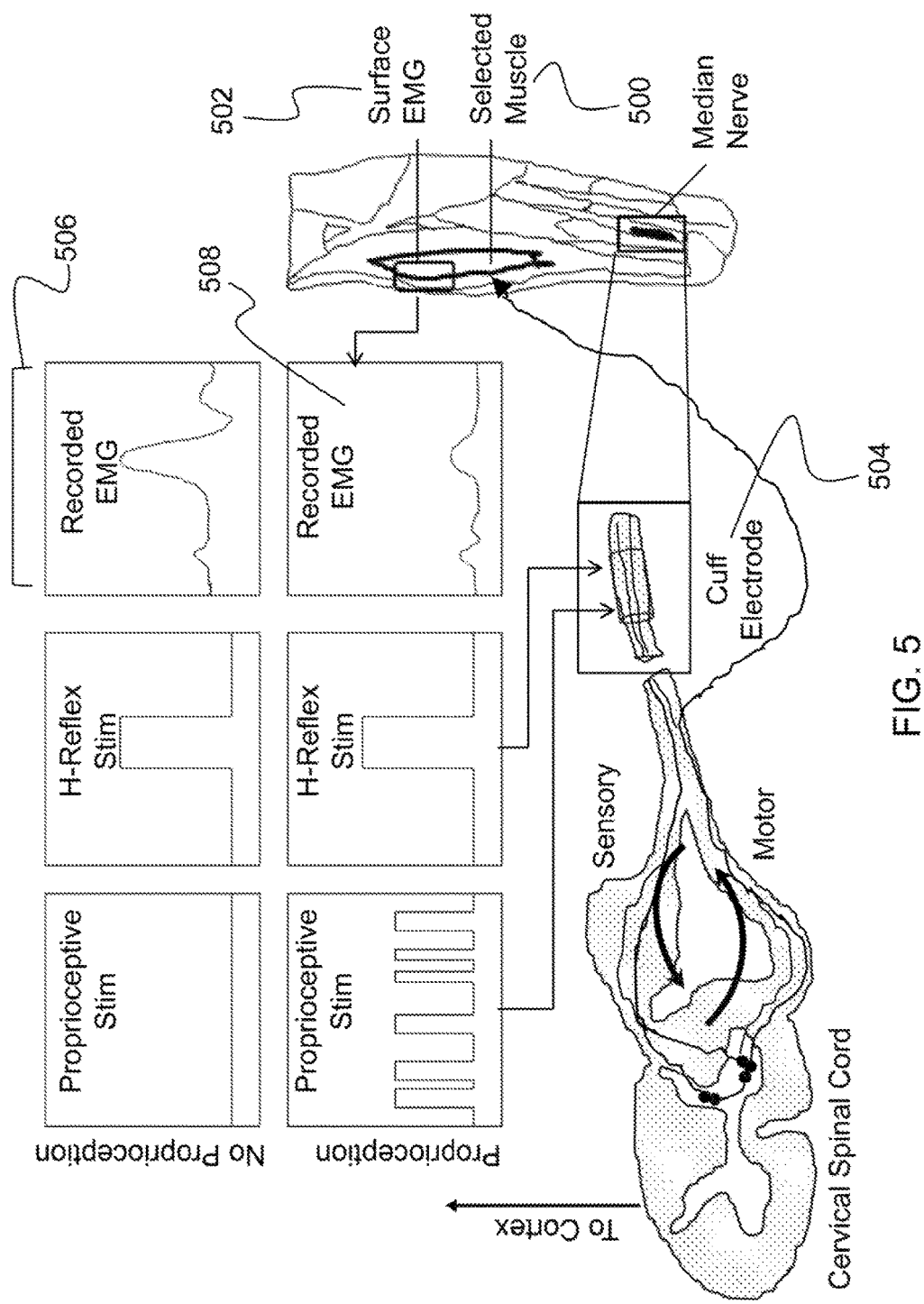
FIG. 5 is an illustration of proprioception altering the response to the H-reflex according to embodiments of the present disclosure.

A key scientific insight is that proprioception alters the response of the Hoffmann's reflex (H-reflex). The H-reflex is a reflectory reaction of muscles after electrical stimulation of type Ia sensory fibers. As shown in FIG. 3, an electrical stimulation pulse that elicits an H-reflex 318 is generated by a stimulation pattern generator 314 and sent to the implanted electrode 308, which then initiates current stimulation of the peripheral nerve, a subset of the human nervous system 306. The stimulation pattern generator 314 provides, on the one hand, a current pattern (element 312, FIG. 6) to stimulate proprioceptive sense and, on the other hand, an H-reflex stimulation, as shown in FIG. 5. There is prior work describing the generation of current patterns used for nerve stimulation by a stimulation pattern generator, such as described in Literature Reference Nos. 14 and 15.

The system described herein uses the resulting H-reflex as an indirect measure to judge if the proprioceptive sensation has been correctly administered and if not, guide the tuning of the nerve stimulation with the help of a spinal cord model, which will be described in further detail below. The current stimulation pattern 312 based on proprioceptive information 300 and the H-reflex stimulation 318 is used in a simulation 320 of the spinal cord model to produce predicted muscle activations 322.

Additionally, a muscle activation sensor 324 (such as a surface electromyogram (sEMG) or EMG implanted within the muscle) generates measured muscle activation 326 data which is sent to the stimulation optimizer 328. Based on the measured muscle activations 326 and the predicted muscle activations 322, a stimulation optimizer 328 determines a change in the current stimulation pattern 330, which is sent to the stimulation pattern generator 314 to automatically adjust the current stimulation pattern 312, as described in detail below.

Figure 4:
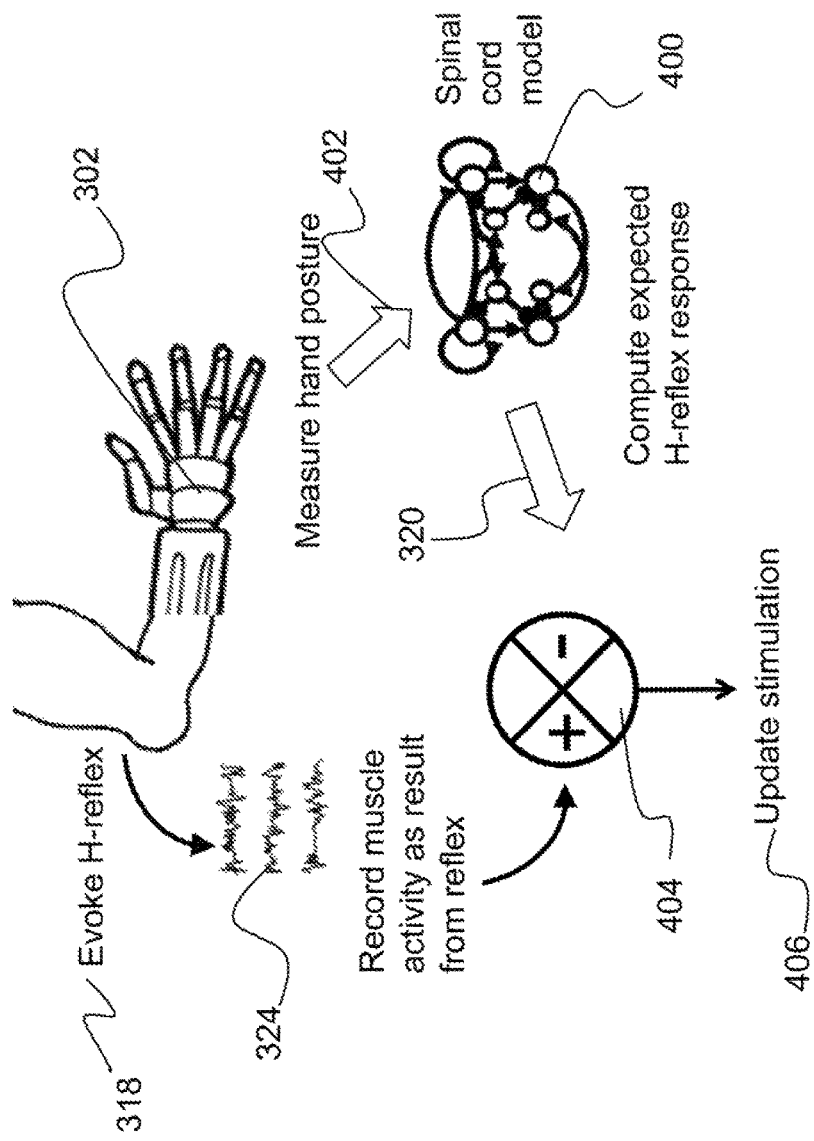
FIG. 4 is an illustration of proprioceptive sense auto-tuning according to embodiments of the present disclosure.

FIG. 4 depicts automatic compensation for any drift in the transfer function between the current stimulation pattern 312 and nerve activation 316 according to embodiments of the present disclosure. The user initiates the auto-tuning when needed. For proprioceptive-sense tuning, the user may trigger a stimulation that evokes an H-reflex stimulation 318 through a button on the prosthesis or a software interface on a computer connected to the prosthesis. The resulting muscle activation 324 from the H-reflex is compared against the predicted activation 320 from a spinal cord model 400, which informs the adaptation of the transfer function.

Research has shown that limb pose and load alters the response of an H-reflex stimulation 318. As shown in FIG. 4, the H-reflex stimulation 318 is evoked, and muscle activity as a result of the H-reflex stimulation 316 is measured (i.e., measured muscle activation 324). As a non-limiting example, electromyography (EMG) can be used to measure the muscle response and compare it with model predictions (i.e., predicted muscle activations 320) from the spinal cord model 400. A measured hand posture, for instance, of the prosthetic limb 302 can be the input to the spinal cord simulation 400 to compute the corresponding expected H-reflex response (or predicted muscle activations 320). To obtain the actual response, in parallel to the proprioceptive stimulation, a second stimulation is administered that triggers the H-reflex (i.e., the H-reflex stimulation). The difference 404 of the measured muscle activations 324 and the predicted muscle activations 320 are processed by the stimulation optimizer 326 to update 406 the current stimulation pattern 312.

The spinal cord model 400 is generated through automated recording and stimulation of the remaining biological circuitry in surviving limbs and muscles, which removes the expert operator from the control loop. This approach allows tuning of the prosthetic outside laboratory settings and obviates the need for expert evaluation, enabling at-home use and maintenance of sophisticated proprioceptive prosthetic devices. Virtually all current approaches to the problem of proprioceptive tuning involve ad-hoc qualitative adjustments performed by human experts. These methods do not take into account the circuit and systems level changes within the physiology that presumably conforms to exploitable principles and rules. Though there has been some evidence for electrophysiological properties of reflexes serving as a state-predictor for neuromuscular performance (see, for example, Literature Reference Nos. 2 and 3), none of these properties have been leveraged to provide tuning-assistance and control-system optimization to prosthetic limbs. The reasons for this lack are two-fold. First, technology has only recently produced the instruments capable of chronic monitoring of the types of biological signals required to generate complex electrophysiological models of neuromechanical systems. Second, sophisticated modeling of the physiological state of a neuromuscular circuit pathway is reliant on expertise that previously has not existed. Though removing the human element from the loop in the prior art has long been a desired element in prosthesis control systems, it has only now become possible to go beyond the prior art. Thus, the invention described herein provides a system and method to automatically tune the stimulation parameters with minimal user intervention to enable at home use of the sensory-feedback prosthesis.

As described above, research has shown that limb pose and load alters the response of an H-reflex stimulation. FIG. 5 depicts this phenomenon, in which afferent proprioception alters the response to the H-reflex stimulation. For proprioceptive sense stimulation, the system according to embodiments of the present disclosure takes advantage of preserved spinal reflex pathways to obtain physiological measures of proprioception. One physiological circuit that is modified by incoming proprioception is the H-reflex. This reflex pathway, which can be stimulated consistently and reliability through single-pulse stimulation of the type Ia afferent fiber of a selected muscle 500, has been shown to be modulated in a stereotypical manner when associated muscle fibers are loaded or stretched prior to stimulation (see Literature Reference Nos. 2 and 5). That is, given proprioceptive input, the H-reflex response is changed in a definable fashion and likely modified as a result of kinematic context. This provides a useful reference point that can verify the accuracy of prosthesis-derived proprioceptive feedback to the biological system. Since this circuitry is contained entirely within the spinal reflex pathway, it can be used as an assessment metric invisibly and automatically during normal use of the prosthesis without the need for time-consuming psychobiological calibration in the laboratory.

While the loss of a limb can damage or eliminate endogenous sensorimotor pathways, it has been demonstrated that, in the human, the H-reflex is preserved in cases of lower-limb amputees (see Literature Reference No. 3). Still, the response of the H-reflex to proprioceptive load may be altered in patients with missing upper limbs, and the specific characteristics of reflex modulation may have to be redefined in human amputee subjects. As a non-limiting example, the response to the H-reflex may be measured with EMG sensors 502 in a laboratory setting with transradially amputated patients.

Making use of the H-reflex muscle response comprises the following steps. In preparation in a laboratory setting, first stimulate the nerve using a single-pulse protocol to identify the proper electrode 504 locales to evoke an H-reflex response on specific muscles (e.g., selected muscle 500). This test will map electrode 504 contacts to specific/selected muscles 500 for proprioceptive feedback. In addition, to find the electrodes stimulating the nerve that correspond to the appropriate proprioceptive sensations, a staircase method of current (312) limits may be used for finding thresholds for sensations for various electrodes on the implanted electrode array 308 (Literature Reference No. 4).

Next, characterize and assess the properties of the H-reflex EMG responses (element 506) under the condition of sensory nerve feedback stimulation to observe how this response is modified as a result of proprioceptive feedback in the laboratory setting. The psychobiological sensation of the proprioceptive feedback is then linked to the modified H-reflex EMG signal 508. Then, the prosthesis user initiates, outside of the laboratory, updates to the stimulation protocol based on this physiological response utilizing the EMG responses and a physiological model-based machine learning algorithm (described in further detail below) that adjusts the sensory stimulation to fit the user's needs.

Figure 6:
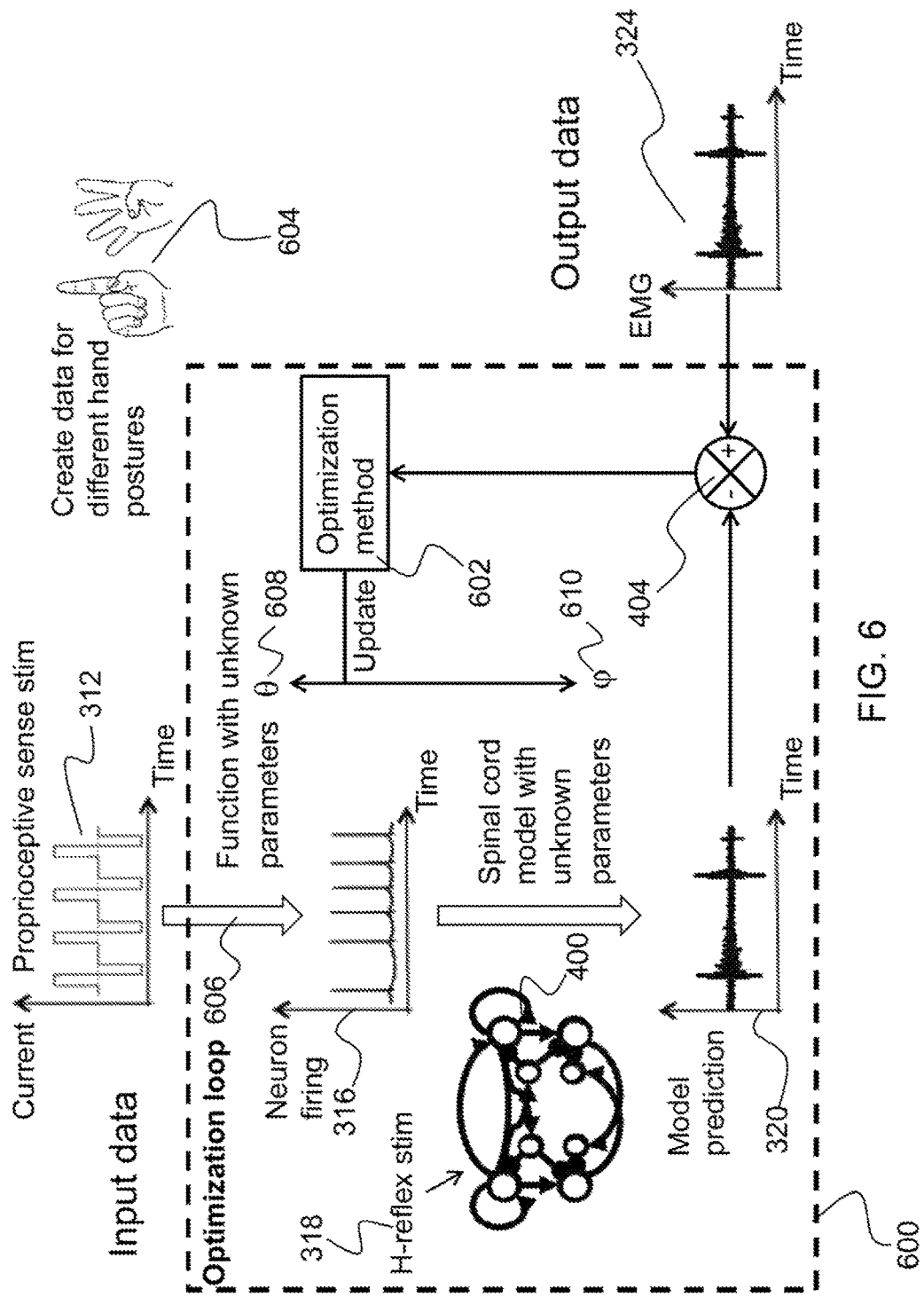
FIG. 6 is an illustration of the transfer function between stimulation and neural activation being indirectly adjusted through a model that predicts the muscle activation of an H-reflex according to embodiments of the present disclosure.

FIG. 6 illustrates how the transfer function between stimulation and neural activation is indirectly adjusted through a model 400 that predicts the muscle activation of an H-reflex stimulation 316 in an optimization loop 600. To auto-adjust stimulation parameters, a function-approximation algorithm is used in combination with the spinal cord model 400 and an optimization method 602.

Initially, a dataset of stimulation patterns and matching H-reflex responses measured through EMG are collected (i.e., create data for different hand postures 604). These data drive the learning of two elements. First, a transfer function 606 between a current stimulation pattern 312 and neural activity on the nerve (element 316), and, second, the spinal cord model 400 that predicts the muscle activation 320 as a response to the neural activity 316 and a separate H-reflex stimulation 318. A non-limiting example of a spinal cord model was described in Literature Reference Nos. 7 and 9.

Both the transfer function 606 and the spinal cord model 400 can be expressed in equations that map in combination the time series of the input stimulus (312) onto EMG data 324. Both equations describing the transfer function 606 and spinal cord model 400 depend on unknown parameters (elements 608 and 610) that are estimated based on the data 324. The parameters are initially computed offline using an optimization method 602 that tries to minimize the error 404 between the predicted EMG (element 320) and the measured EMG (element 324) over a time window (e.g., 1 minute during which the proprioceptive sense stimulation was applied). Several off-the-shelf methods are available for this optimization, such as the Powell's method (Literature Reference No. 11) or Simulated Annealing (Literature Reference No. 12). An important consideration for the choice of method is that the optimization may need to cope with local minima that are not globally optimal. For example, gradient descent methods find solutions that are optimal within a local area of the parameter space but may not be globally optimal for the entire parameter space. Therefore, other methods, such as Simulated Annealing, may be required.

Once the prosthetic limb (prosthesis) is in use, the spinal cord model 400 and transfer function 606 are adapted based on novel data. The user generates these data by moving the prosthesis into two or three pre-specified postures and pressing a button on the prosthesis that triggers the H-reflex stimulation 318. Since the parameter space is high dimensional, a fast and reliable way to optimize the parameters to the novel data is needed. To facilitate the optimization, the initial data set (collected as described above) is used to compute a two-dimensional parameter subspace that maximally describes the impact on the H-reflex response. A non-limiting method to compute such a subspace is principal component analysis (Literature Reference No. 13). Then, drift is adapted to by changing parameters only on this low-dimensional subspace. A method to quickly adapt to a drift of a functional relationship was described in Literature Reference No. 6. This approach allows the drift in the transfer function between electric stimulation and neural firing to be captured. Without the spinal cord model 400 and the H-reflex, there would not be access to the neural firing. Once this drift is captured, the transfer function between the current stimulation pattern 312 and the neural activation (element 316) can be automatically adjusted, and given this function the appropriate stimulation 312 for a desired activation 316 can be computed. The desired activation can be obtained from the initial data collected in the laboratory as described above.

In summary, the present invention provides a system and method to calibrate a sensor-neural interface of a prosthetic limb. Particularly, the system according to embodiments of the present disclosure addresses the challenge of providing and maintaining proprioceptive feedback about the state of the prosthetic limb. Proprioception is the sense of the position and posture of parts of the body. In the present invention, proprioceptive feedback is provided by administering a stimulating current to a nerve. A key scientific insight is that proprioception alters the response of the H-reflex. The H-reflex is a reflexory reaction of muscles after electrical stimulation of type Ia sensory fibers. The system described herein uses the H-reflex as an indirect measure to judge if the proprioceptive sensation has been correctly administered by comparing the measured response to the expected response with help of a spinal cord model. In case of a mismatch, the nerve stimulation pattern for the proprioceptive feedback is adjusted accordingly.

The system according to embodiments of the present disclosure can support the recovery of any person, including veterans, who has lost a limb or lost the ability to naturally perceive proprioceptive feedback. This system may be also used to enhance proprioceptive sensation in healthy individuals (e.g., for applications requiring highly accurate body control).

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A system for automatically tuning the sensory feedback of a prosthetic device, the system comprising:
    an implantable electrode configured to administer a stimulus to a peripheral nerve of a user wearing a prosthetic device, the stimulus configured to evoke a muscle response in the user;
    a muscle activation sensor configured to measure the muscle response; and
    one or more processors and a memory, the memory being a non-transitory computer-readable medium having executable instructions encoded thereon, such that upon execution of the instructions, the one or more processors are configured to perform operations of:
    applying a current stimulation pattern to the electrode, the current stimulation pattern corresponding to a position of a prosthetic device of the user;
    using the muscle activation sensor to detect the measured muscle response to the current stimulation pattern;
    determining a predicted muscle activation using the current stimulation pattern and the posture of the prosthetic device using a spinal cord model; and
    using the measured muscle response and predicted muscle activations to dynamically determine an adjusted stimulation pattern configured to compensates for a neuroplastic or hardware change.

2. The system as set forth in claim 1, wherein the stimulus evoking the muscle response is configured to evoke a Hoffmann's reflex.

3. The system as set forth in claim 1, wherein when the user moves the prosthetic device into a predetermined posture the device is further configured to allow the user to apply the stimulus that evokes the muscle response.

4. The system as set forth in claim 3, wherein the stimulus evoking the muscle response is configured to evoke a Hoffmann's reflex.

5. A computer implemented method for automatically tuning the sensory feedback of a prosthetic device, the method comprising:
    causing one or more processors to execute instructions encoded on a nontransitory computer-readable medium, such that upon execution, the one or more processors perform operations of:
    applying a current stimulation pattern to an implantable electrode, the current stimulation pattern configured to corresponding to a posture of a prosthetic device of a user;
    using a muscle activation sensor to detect a measured muscle response to the current stimulation pattern;
    determining a predicted muscle activation using the current stimulation pattern and the posture of the prosthetic device using a spinal cord model; and
    using the measured muscle response and the predicted muscle activations to dynamically determining an adjust stimulation pattern that compensates for neuroplastic or hardware changes.

6. The method as set forth in claim 5, wherein the stimulus evoking the muscle response is configured to evoke a Hoffmann's reflex.

7. The method as set forth in claim 5, wherein when the user moves the prosthetic device into a predetermined posture the device is further configured to allow the user to apply the stimulus that evokes the muscle response.

8. The method as set forth in claim 7, wherein the stimulus evoking the muscle response is configured to evoke a Hoffmann's reflex.

9. A computer program product for automatically tuning the sensory feedback of a prosthetic device, the computer program product comprising:
    a non-transitory computer-readable medium having executable instructions encoded thereon, such that upon execution of the instructions by one or more processors, the one or more processors perform operations of:
    applying a current stimulation pattern to an implantable electrode, the current stimulation pattern configured to corresponding to a posture of a prosthetic device of a user;
    using a muscle activation sensor to detect a measured muscle response to the current stimulation pattern;
    determining a predicted muscle activation using the current stimulation pattern and the posture of the prosthetic device using a spinal cord model; and
    using the measured muscle response and the predicted muscle activations to dynamically determining an adjust stimulation pattern that compensates for neuroplastic or hardware changes.

10. The computer program product set forth in claim 9, wherein the stimulus evoking the muscle response is configured to evoke a Hoffmann's reflex.

11. The computer program product set forth in claim 9, wherein when the user moves the prosthetic device into a predetermined posture the device is further configured to allow the user to apply the stimulus that evokes the muscle response.

12. The computer program product set forth in claim 11, wherein the stimulus evoking the muscle response is configured to evoke a Hoffmann's reflex.

* * * * *